United States Patent [19]

Patel et al.

[11] 4,379,079

[45] Apr. 5, 1983

[54] USE OF METHYL-THIO-2-METHYL-2-PENTENOATE IN AUGMENTING OR ENHANCING THE AROMA OF PERFUME COMPOSITIONS, COLOGNES AND PERFUMED ARTICLES

[75] Inventors: Raman R. Patel, Plainsboro; Alan O. Pittet, Atlantic Highlands; Ranya Muralidhara, Fair Haven, all of N.J.

[73] Assignee: International Flavors & Fragrances Inc., New York, N.Y.

[21] Appl. No.: 322,843

[22] Filed: Nov. 19, 1981

[51] Int. Cl.$^3$ ............................ A61K 7/46; C11B 9/00
[52] U.S. Cl. .................................. 252/522 R; 252/8.6; 252/89.1; D28/4
[58] Field of Search ................ 260/455 R; 252/522 R

[56] References Cited

U.S. PATENT DOCUMENTS

| | | | |
|---|---|---|---|
| 3,161,672 | 12/1964 | Zachry et al. | 260/455 R |
| 3,879,562 | 4/1975 | Pittet et al. | 260/455 R |
| 3,904,556 | 9/1975 | Pittet et al. | 260/455 R X |
| 3,907,718 | 9/1975 | Hall et al. | 252/522 R |
| 3,948,816 | 4/1976 | Helmlinger et al. | 252/522 R |
| 3,966,799 | 6/1976 | Hall et al. | 252/522 R |
| 3,978,239 | 8/1976 | Hall et al. | 252/522 R |
| 4,000,327 | 12/1976 | Tseng et al. | 252/522 R |
| 4,126,585 | 11/1978 | Conrad et al. | 252/522 R |

FOREIGN PATENT DOCUMENTS 542641  1/1942  United Kingdom ............ 252/522 R

*Primary Examiner*—Helen M. S. Sneed
*Attorney, Agent, or Firm*—Arthur L. Liberman

[57] ABSTRACT

Described are cis isomers, trans isomers and mixtures of cis and trans isomers of methyl-thio-2-methyl-2-pentenoate defined according to one of the structures:

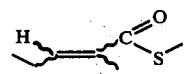

wherein the wavy lines represent "cis" and "trans" configurations of methyl, ethyl and methylthiocarboxy moieties around the carbon-carbon double bond;

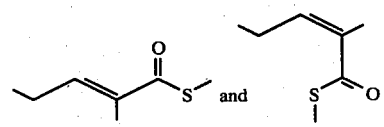

and uses of such methyl-thio-2-methyl-2-pentenoates in augmenting or enhancing the aroma of perfume compositions, colognes and perfumed articles such as solid or liquid anionic, cationic, nonionic or zwitterionic detergents, fabric softener compositions, fabric softener articles and optical brighteners and perfumed polymer compositions.

5 Claims, 2 Drawing Figures

GLC PROFILE FOR FRACTION 7 OF EXAMPLE I.

IR SPECTRUM FOR EXAMPLE I

USE OF METHYL-THIO-2-METHYL-2-PENTENOATE IN AUGMENTING OR ENHANCING THE AROMA OF PERFUME COMPOSITIONS, COLOGNES AND PERFUMED ARTICLES

BACKGROUND OF THE INVENTION

This invention relates to methyl-thio-2-methyl-2-pentenoate derivatives which are defined according to one of the structures:

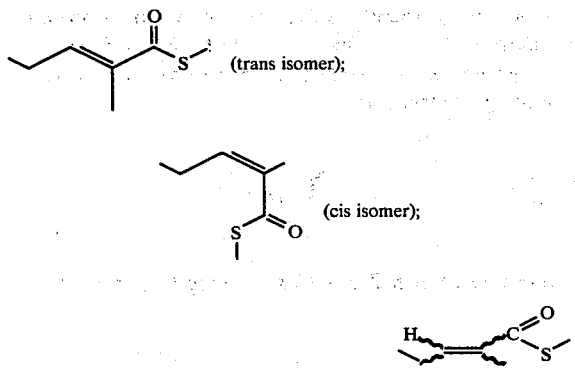

(representative of cis and/or trans isomers) wherein the wavy lines represent moieties juxtaposed around the carbon-carbon double bond, and uses thereof in augmenting or enhancing the aroma of perfume compositions, colognes and perfumed articles.

There has been considerable work performed relating to substances which can be used to impart (or enhance) aromas to (or in) various consumable materials. These substances are used to diminish the use of natural materials, some of which may be in short supply and to provide more uniform properties in the finished product. Warm fruity, bready, yeast-like, strawberry-like fragrance nuances are desirable in perfume compositions, perfumed articles and colognes.

Thioesters in particular are well known for use in augmenting or enhancing the organoleptic properties of consumable materials. Thus, thioesters for use in the flavoring of foodstuffs are disclosed in U.S. Pat. No. Re. 30,370 wherein compounds having the generic structure:

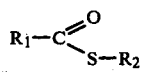

wherein $R_1$ and $R_2$ are alkyl or alkenyl, for example, allyl thiopropionate having the structure:

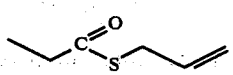

are disclosed as being useful for meaty flavors.

Unsaturated alkenoic acid esters (containing the oxygen rather than the sulfur atom) are also known in augmenting or enhancing the aroma or taste of consumable materials including strawberry fragrances and strawberry flavored foodstuffs, for example, those disclosed in United States Letters Patent, Ser. No. 3,931,293, for example, the compound having the structure:

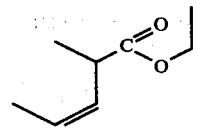

and corresponding trans isomers and mixtures of same having a high "cis" isomer content.

Furthermore, $C_1$-$C_6$ alkyl-2-methyl-3,4-pentadienoates are disclosed in U.S. Pat. No. 4,094,823 to be useful in augmenting or enhancing the berry, chamomile, wormwood, apple and/or pineapple notes of perfume compositions, colognes and perfumed articles.

Nothing in the prior art discloses the compounds of our invention, the methyl-thio-2-methyl-2-pentenoates as related to the use of same in augmenting or enhancing the aroma of perfume compositions, colognes and perfumed articles.

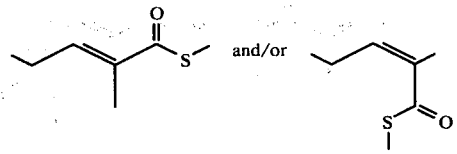

Figure 1:
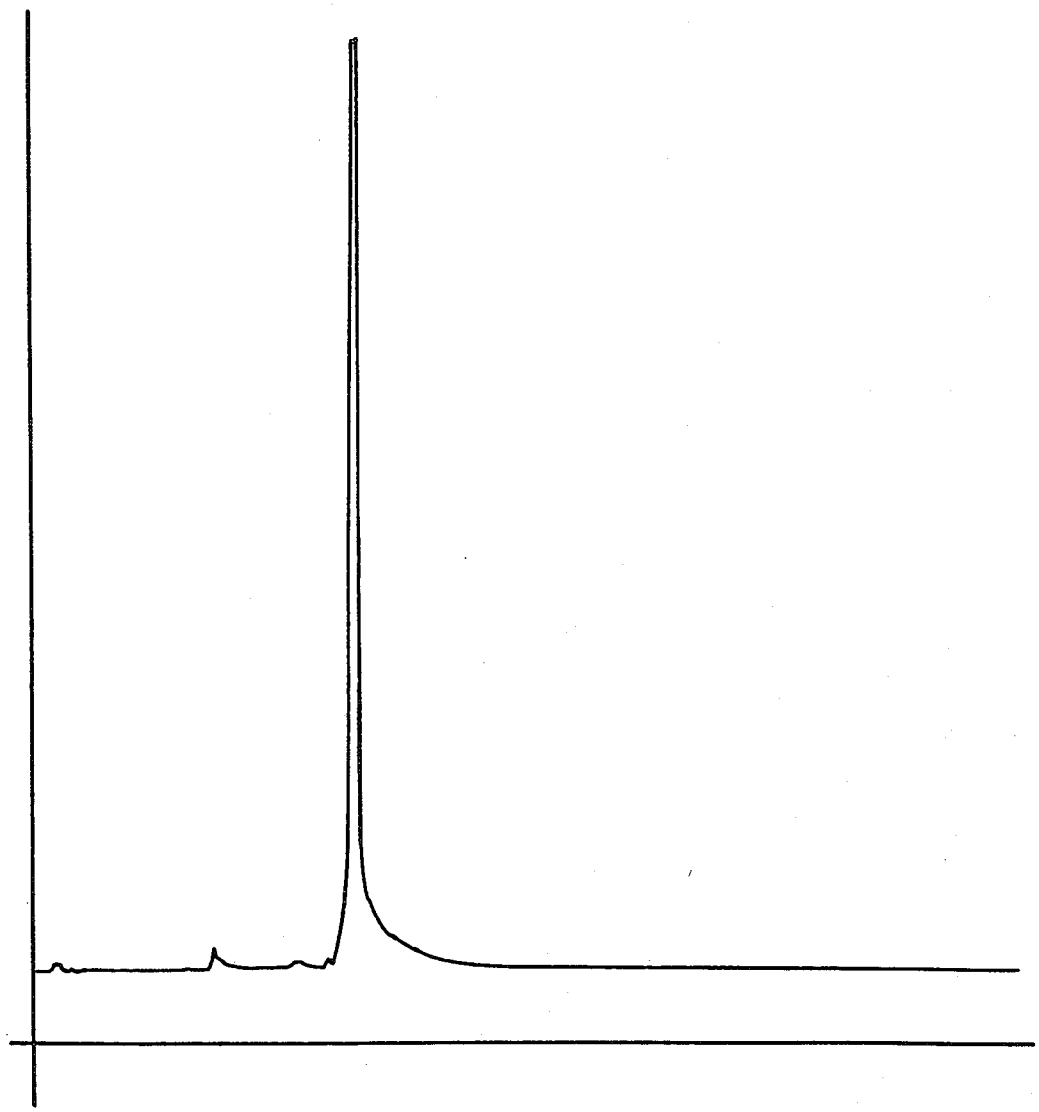
FIG. 1 is the GLC profile for fraction 7 of the distillation product of the reaction product of Example I containing the compounds having the structures.
Figure 2:
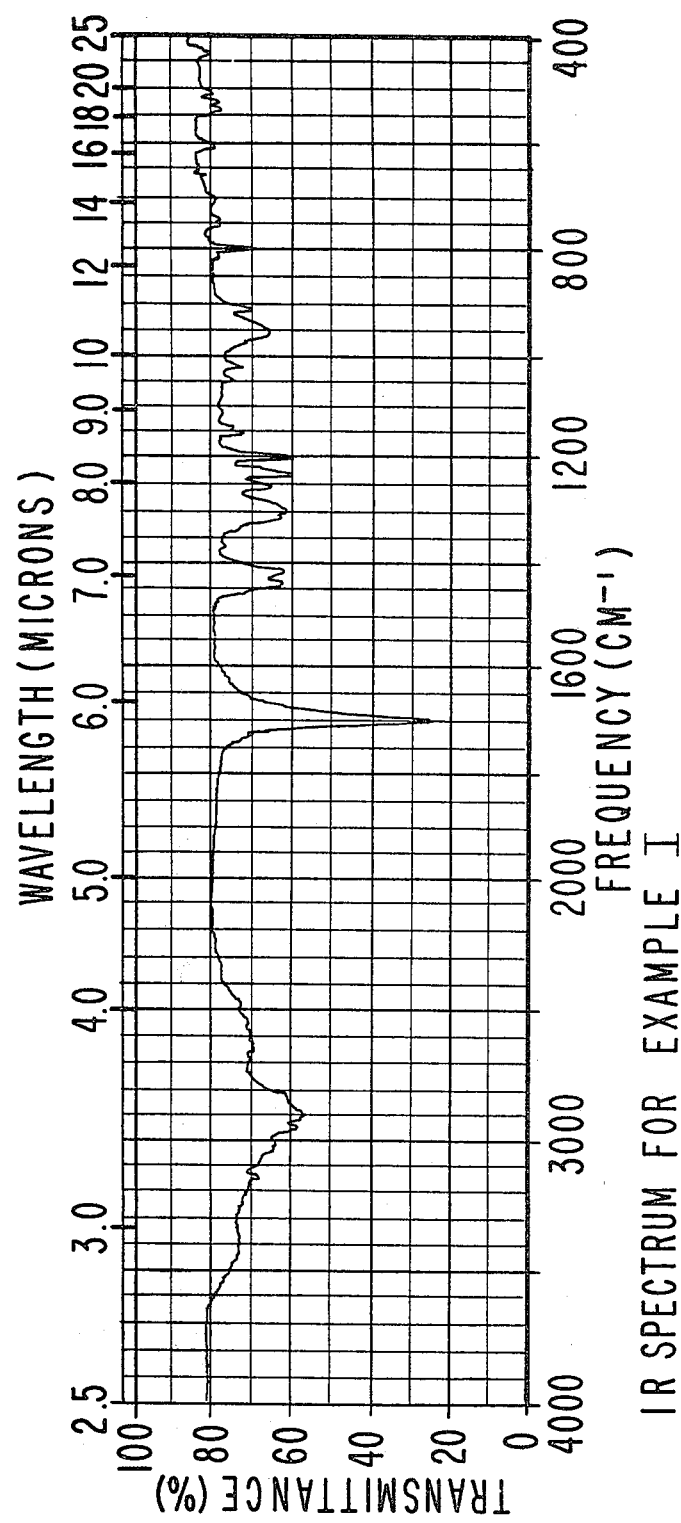

FIG. 2 is the NMR spectrum for peak 1 of the GLC profile of FIG. 1 which is the GLC profile for fraction 7 of the distillation product of the reaction product of Example 1 containing the compounds having the structures:

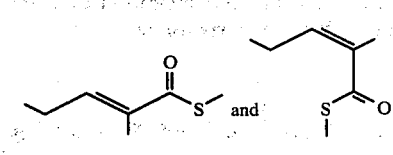

THE INVENTION

It has been determined that certain methyl-thio-2-methyl-2-pentenoate compounds defined according to one of the structures:

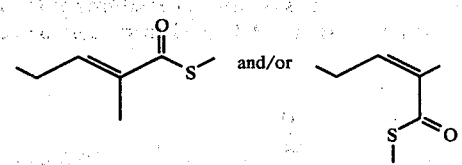

or defined according to the generic structure:

wherein the wavy lines represent "cis" or "trans" configurations of ethyl, methyl, hydrogen or methylthiocarboxy moieties around the carbon-carbon double bond are capable of imparting a variety of flavors to various consumable materials such as foodstuffs, chewing gums, toothpaste and medicinal products.

The compounds of our invention defined according to the structures:

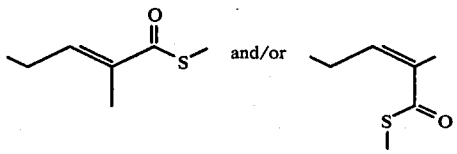

around the carbon-carbon double bond are capable of imparting (or augmenting or enhancing) a variety of aroma nuances to (or in) various consumable materials such as perfume compositions, colognes and perfumed articles (e.g., solid or liquid anionic, cationic, nonionic or zwitterionic detergents, fabric softeners, drier-added fabric softener articles, e.g., BOUNCE ® or CLING-FREE ®), optical brightener compositions, or perfumed polymer compositions.

The compounds of our invention defined according to the structures:

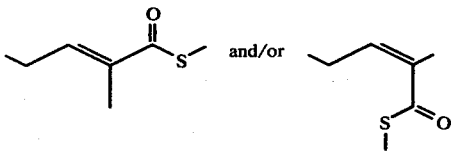

are useful in augmenting, enhancing or imparting the aroma of perfume compositions, colognes or perfumed articles whereby warm fruity, bready, yeast-like, strawberry-like aroma nuances are imparted, enhanced and/or augmented.

The compounds of our invention defined according to one or both of the structures:

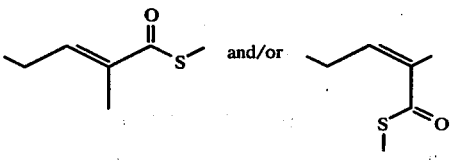

may be prepared by first reacting 2-methyl-2-pentenoic acid (the cis or trans isomers or mixtures of the cis and trans isomers as desired) defined according to one of the structures:

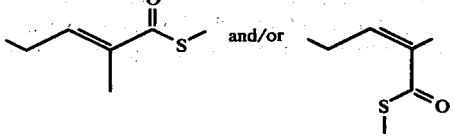

with a halogenating agent defined according to the structure:

$$ZX_n$$

wherein Z represents phosphorous, phosphorous oxy having the structure:

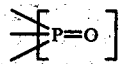

or sulfoxy having the structure:

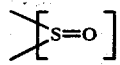

wherein n is the integer 2, 3 or 5; wherein X represents chloro or bromo; wherein n is 3 or 5 when Z represents phosphorous; n is 3 when Z represents phosphorous oxy having the structure:

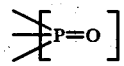

and n is 2 when Z is sulfoxy having the structure:

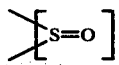

to form the alkenoyl halide defined according to the structure:

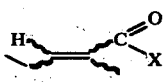

wherein the wavy lines are defined as above.

The resulting alkenoyl halide or mixture of cis and trans alkanoyl halides is then reacted with methyl mercaptan in order to form the compounds of our invention defined according to the structures:

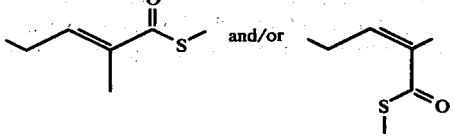

or defined according to the structure:

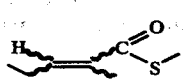

wherein the wavy lines are defined, supra.

The reaction defined aforementioned may be graphically illustrated as follows:

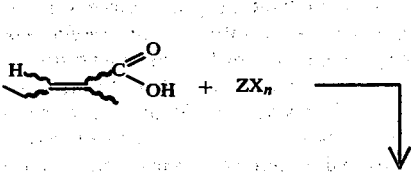

-continued

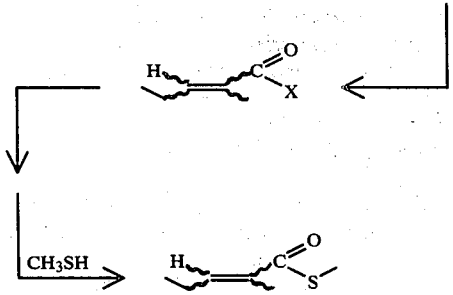

The reaction of the 2-methyl-2-pentenoic acid defined according to the structure:

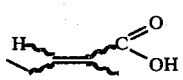

with the compound defined according to the structure:

ZX$_n$ for example, thionyl chloride (SOCl$_2$) phosphorous pentachloride, phosphorous oxychloride (POCl$_3$) or phosphorous trichloride takes place in the presence of an inert solvent such as toluene or benzene or xylene at reflux conditions. Thus, in the case of using a toluene solvent, it is preferable that the reaction be carried out at a temperature in the range of 50°–110° C. depending on the quantity of toluene in the reaction mass, preferably and expeditiously the reaction takes place at atmospheric pressure although pressures greater than atmospheric may be used with higher temperatures of reaction and shorter time periods of reaction. Preferably the mole ratio of the compound having the structure:

ZX$_n$ the 2-methyl-2-pentenoic acid having the structure:

is 1:1. In order to insure that all of the 2-methyl-2-pentenoic acid is reacted, a slight excess of the compound having the structure:

ZX$_n$ may be used. Thus, if thionyl chloride, phosphorous oxychloride, phosphorous trichloride or phosphorous pentachloride is used and a slight excess of same is used, the excess phosphorous trichloride, phosphorous oxychloride, phosphorous pentachloride or thionyl chloride may subsequently be hydrolyzed or neutralized after the second reaction of the alkenoyl halide having the structure:

with methyl mercaptan.

Thus, in the reaction of methyl mercaptan with the alkenoyl halide having the structure:

wherein X is chloro or bromo, it is preferable that the reaction temperature be between −10° C. and 0° C. It is also preferable that the mole ratio of methyl mercaptan:alkenoyl halide defined according to the structure:

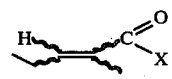

be about 1:1 and if any excess of any reagent is used, that excess be in favor of the methyl mercaptan. The reaction between the methyl mercaptan and alkenoyl halide defined according to the structure:

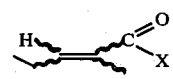

also is to take place in the presence of an inert solvent such as benzene, toluene or xylene. Conveniently, the same solvent as used in the first reaction between the compound having the structure:

ZX$_n$ and the 2-methyl-2-pentenoic acid having the structure:

is used. Thus, if toluene is used in the first reaction, then conveniently, the same toluene may be used in the second reaction.

At the end of the reaction, the reaction mass is heated up in order to evolve any excess volatiles, e.g. excess methyl mercaptan and in order to evolve products of reaction, e.g. hydrogen chloride, sulfur dioxide or the like.

The reaction mass is then "worked up" by first cooling to room temperature and then washing the reaction mass with water and finally drying over an anhydrous inert drying agent such anhydrous sodium sulfate. The reaction mass is then distilled to yield product distilling at a vapor temperature of about 95°–98° C. and a pressure of 5 mm/Hg or an equivalent distillation temperature and pressure.

It will thus be appreciated from the present disclosure that the methyl-thio-2-methyl-2-pentenoates of our invention can be used to alter, augment, enhance or impart the aroma of a wide variety of materials such as perfume compositions, colognes and perfumed articles.

Thus, one or both of the methyl-thio-2-methyl-2-pentenoates and in auxiliary perfume ingredient, including, for example, alcohols, aldehydes, nitriles, esters, cyclic esters, thio esters other than the methyl-thio-2-methyl-2-pentenoates of our invention, cyclic esters, natural essential oils and hydro carbons may be admixed so that the combined odors of the individual components produce a pleasant and desired fragrance, particularly and preferably in strawberry fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, the individual component will contribute its particular olfactory characteristics, but the over-all effect of the perfume composition will be the sum of the effects of each of the ingredients and the action of the effect of each of the ingredients on each other. Thus, one or both of the methyl-thio-2-methyl-2-pentenoates of our invention can be used to alter the aroma characteristics of a perfume composition, for example, by utilizing or moderating the olfactory reaction contributed by another ingredient in the composition.

The amount of one or both of the methyl-thio-2-methyl-2-pentenoates of our invention which will be effective in perfume compositions depends on many factors, including the other ingredients, their amounts and the effects which are desired. It has been found that perfume compositions containing as little as 0.3% of one or both the methyl-thio-2-methyl-2-pentenoate derivatives or even less (e.g., 0.05%) can be used to impart a scent odor to soaps, cosmetics or solid or liquid anionic, cationic, nonionic or zwitterionic detergents, fabric softener compositions, drier-fabric softener articles such as BOUNCE® or CLING-FREE® or other perfumed articles. The amount employed can range up to 5% of the fragrance components in the perfume composition and will depend on considerations of cost, nature of the end product, the effect desired on the finished product and the particular fragrance sought.

One or both of the methyl-thio-2-methyl-2-pentenoates of our invention are useful in perfume compositions or taken alone as an olfactory component in detergents (e.g., solid or liquid anionic, cationic, nonionic or zwitterionic detergents) and soaps, space odorants and deodorants, perfume compositions, colognes, toilet waters, bath preparations, such as bath oils, and bath solids; hair preparations, such as lacquers, brilliantines, pomades and shampoos; costmetic preparations, such as creams, deodorants, hand lotions and sun screens; powders, such as talcs, dusting powders, face powders; polymer/perfume blends and the like.

When used as an olfactory component of a perfumed article, as little as 100 parts per million of one or both of the methyl-thio-2-methyl-2-pentenoates of our invention will suffice to impart, augment or enhance a warm fruity, bready, yeast-like, strawberry-like aroma character which is one of the key odor characteristics of strawberry perfume formulations. Generally, no more than 2.0% of one or both of the methyl-thio-2-methyl-2-pentenoates of our invention based on the ultimate end product perfumed article is required in the perfumed article.

In addition, the perfume composition or fragrance composition or methyl-thio-2-methyl-2-pentenoate when incorporated individually into a perfumed article of our invention can contain a vehicle, or carrier for said methyl-thio-2-methyl-2-pentenoate. The vehicle can be a liquid such as an alcohol, e.g., ethanol, a non-toxic glycol, e.g., propylene glycol or the like. The carrier can also be an absorbent solid, such as a gum (e.g., gum arabic, zan tham gum or guar gum) or components for encapsulating the composition (such as gelatin when encapsulation is carried out by coacervation; or urea formaldehyde resins when encapsulation is carried out by forming a polymeric capsule around the liquid perfume composition center).

The following Example I is given to illustrate a technique for producing the methyl-thio-2-methyl-2-pentenoate derivatives of our invention. The following Examples II and on wards are given to illustrate embodiments of our invention as it is presently preferred to practice with respect to the utilities of the methyl-thio-2-methyl-2-pentenoate derivatives of our invention in perfume compositions, colognes and perfumed articles.

It will be understood that these examples are illustrative and the invention is not to be considered as being restricted thereto except as indicated in the appended claims.

EXAMPLE I

Preparation of Methyl-thio-2-methyl-2-pentenoates

Reactions:

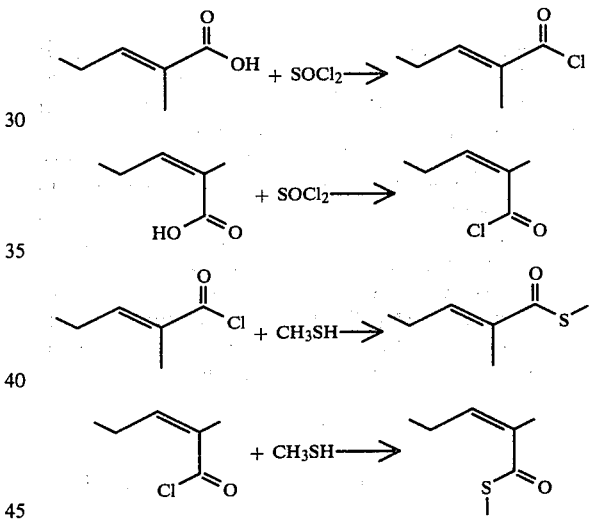

Into a 2 liter reaction flask equipped with heating mantle, cooling bath, stirrer, thermometer, addition funnel, reflux condenser, nitrogen blanket apparatus, dry trap and caustic trap for recovery of hydrogen chloride and sulfur dioxide gasses are placed 200 ml toluene followed by 150 grams (1.82 moles) of 2-methyl-2-pentenoic acid.

While maintaining the temperature of the resulting mixture at 23° C. over a period of 20 minutes, 173 grams (1.45 moles) of thionyl chloride is added to the reaction mass.

The reaction mass is then slowly heated to reflux and while refluxing the reaction mass over a period of 1 hour while maintaining the temperature at 62°-63° C., a small amount of hydrogen chloride and sulfur dioxide is evolved.

At the end of the 1 hour period, GLC analysis indicates the completion of the reaction. The reaction mass is then cooled to −5° C.

While maintaining the reaction mixture at a temperature of −4°−−5° C., 104 grams (2.20 moles) of methyl mercaptan is added to the reaction mixture over a period of 30 minutes. At the end of the addition of the methyl mercaptan, the reaction mass is heated to room temperature (24° C.). Excess methyl mercaptan is then evolved. The reaction mass is heated at 30° C. for a period of 1 hour.

The reaction mass is then added to a separatory funnel containing 250 ml of water and the phases are allowed to separate.

The organic phase is then washed with an additional 250 ml of water. The organic phase is then dried over anhydrous sodium sulfate and the resulting mixture is then filtered and distilled on a 1" Goodloe column yielding the following fractions:

| Fraction Number | Vapor Temp. (°C.) | Liquid Temp. (°C.) | Pressure mm/Hg. |
|---|---|---|---|
| 1 | 25/35 | 35/61 | 7/10 |
| 2 | 51 | 75 | 7 |
| 3 | 67 | 88 | 7 |
| 4 | 73 | 94 | 7 |
| 5 | 91 | 105 | 5 |
| 6 | 96 | 138 | 5 |
| 7 | 90 | 180 | 5 |

Fractions 6 and 7 are bulked and evaluated for their organoleptic properties.

Bulked fractions 6 and 7 have a warm fruity, bready, yeast-like aroma characteristic with intense strawberry undertones.

The bulked fractions 6 and 7 are a mixture of cis and trans isomers having the structures:

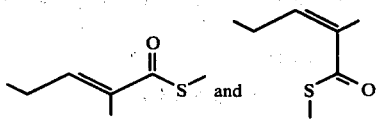

as confirmed by NMR, IR and mass spectral analyses.

FIG. 1 is the GLC profile for fraction 7. Peak "1" on FIG. 1 represents a mixture of cis and trans isomers having the structures:

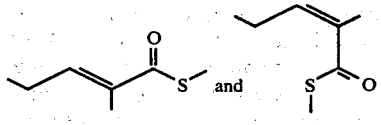

FIG. 2 is the NMR spectrum for peak "1" of the GLC profile of FIG. 1.

EXAMPLE II

Strawberry Fragrance

The following mixture is prepared:

| Ingredient | Parts by Weight |
|---|---|
| Cuminic acetate | 15.0 |
| Ethyl acetoacetate | 3.0 |
| Ethyl laurate | 30.0 |
| Cinnamyl isobutyrate | 15.0 |
| Cinnamyl decylate | 20.0 |
| Diacetyl (10% in 95% aqueous ethanol) | 2.0 |
| Ethyl pelargonate | 5.0 |

| Ingredient | Parts by Weight |
|---|---|
| Gamma undecalactone | 20.0 |
| Ethyl isobutyrate | 110.0 |
| Ethyl isovalerate | 60.0 |
| Ethyl heptanoate | 12.0 |
| Dulcinyl | 5.0 |
| 2(para-hydroxyphenyl)-3-butanone | 2.0 |
| Ethyl acetate | 5.0 |
| Beta-ionone | 5.0 |
| Palatone | 3.0 |
| Vanillin | 10.0 |
| Ethyl vanillin | 10.0 |
| Ethyl-3-methyl-3-phenyl glycidate | 70.0 |
| Methyl-thio-2-methyl-2-pentenoate, bulked distillation fraction 6 and 7 prepared according to the process of Example I | 15.0 |

The mixture containing the methyl-thio-2-methyl-2-pentenoates prepared according to Example I (bulked fractions 6 and 7) imparts a warm fruity, bready, yeast-like aroma characteristic necessary to create a "natural effect" to the strawberry aroma.

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Methyl-thio-2-methyl-2-pentenoate mixture prepared according to Example I, bulked fractions 6 and 7. | A warm fruity, bready, yeast-like aroma with strawberry topnotes. |
| Fragrance formulation of Example II. | An intense strawberry aroma with warm fruity, bready and yeast-like topnotes. |

EXAMPLE IV

Perfumed Liquid Detergents

Concentrated liquid detergents (Lysine salt of n-dodecylbenzene sulfonic acid as more specifically described in U.S. Pat. No. 3,948,818, issued on Apr. 6, 1976 incorporated by reference herein) with aroma nuances as set forth in Table I of Example III are prepared containing 0.10%, 0.15%, 0.20%, 0.25%, 0.30% and 0.35% of the substance set forth in Table I Example III. They are prepared by adding and homogeneously mixing the appropriate quantity of substance set forth in Table I of Example III in the liquid detergent. The detergents all possess excellent aromas as set forth in Table I of Example III intensity increasing with greater concentrations of substance as set forth in Table I of Example III.

EXAMPLE V

Preparation of Colognes and Handkerchief Perfumes

Compositions as set forth in Table I of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III are imparted to the colognes and to the handkerchief perfumes at all levels indicated.

EXAMPLE VI

Preparation of Soap Compositions

One hundred grams of soap chips [per sample] (IVORY ®, produced by the Proctor & Gamble Company of Cincinnati, Ohio), are each mixed with one gram samples of substances as set forth in Table I of Example III until Homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "Neodol ® 45-11" (a $C_{14}$–$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and ther perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table I of Example III.

Fabric softening compositions prepared according to Example I at column 15 of U.S. Pat. No. 3,632,396 having aroma characteristics as set forth in Table I of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table I of Example III, supra.

EXAMPLE IX

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example III supra | 0.10 weight percent |

The perfuming substances as set forth in Table I of Example III add aroma characteristics as set forth in Table I of Example III which are rather intense and aesthetically pleasing to the users of the soft-feel, good-hold pump hair sprays.

EXAMPLE X

Conditioning Shampoos

Monamid CMA (prepared by the Mona Industries Company) (3.0 weight percent) is melted with 2.0 weight percent coconut fatty acid (prepared by Proctor & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ® 755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 wt ratio of A:B and cooled to 45° C. and 0.3 wt percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

EXAMPLE XI

A fabric conditioner produced according to the method of U.S. Pat. No. 4,291,072 issued on Sept. 22, 1981 is produced whereby the sheet consisting of nonwoven rayon substrate as set forth at column 3, lines 25-34 passed through the bath of molten cationic fabric softener-isopropenyl mixture is passed through the bath at 10 atmospheres pressure, during which time a fragrance material as set forth in Table I of Example III is added at the rate of 0.35%. The resulting sheet when used with a clothing batch gives rise to a pleasant aroma in the head space above the clothing batch as set forth in Table I of Example III.

What is claimed is:

1. A process for augmenting or enhancing the aroma of consumable materials selected from the group consisting of perfume compositions, colognes and perfumed articles comprising the step of intimately admixing with a perfume composition base, a cologne base or a perfumed article base, an aroma augmenting or enhancing quantity of a methyl-thio-2-methyl-2-pentenoate defined according to the structure:

wherein the wavy lines represent covalent bonds juxtaposed in a "cis" or "trans" configuration around the carbon-carbon double bond of the structure.

2. The process of claim 1 wherein the methyl-thio-2-methyl-2-pentenoate has the structure:

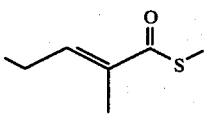

3. The process of claim 1 wherein the methyl-thio-2-methyl-2-pentenoate has the structure:

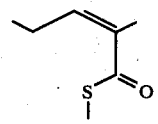

4. The process of claim 1 wherein the methyl-thio-2-methyl-2-pentenoate is a mixture of compounds having the structures:

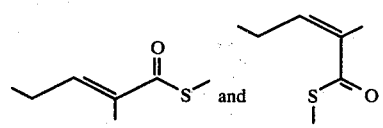

5. The process of claim 1 wherein the consumable material is a perfume composition or cologne.

* * * * *